United States Patent [19]

Nakao et al.

[11] Patent Number: 4,462,136
[45] Date of Patent: Jul. 31, 1984

[54] DENTAL IMPLEMENT FOR REMOVING PLAQUE AND MASSAGING GUMS

[75] Inventors: Shunichi Nakao, Sakado; Motonori Yamauchi, Yokosuka; Churyo Suzuki, Ichikawa, all of Japan

[73] Assignees: Showa Jakuhin Kako Co., Ltd.; Tokyo Boshi Kabushiki Kaisha, both of Japan

[21] Appl. No.: 319,605

[22] Filed: Nov. 9, 1981

[30] Foreign Application Priority Data

Nov. 18, 1980 [JP] Japan ................ 55-162346

[51] Int. Cl.³ .................. A46B 9/04; A61C 15/00
[52] U.S. Cl. .................. 15/167 R; 15/110; 15/159 A; 15/104.92; 132/89
[58] Field of Search ........... 15/167 R, 159 A, 104.93, 15/104.92, 110; 132/89-93

[56] References Cited

U.S. PATENT DOCUMENTS

| | | | |
|---|---|---|---|
| 2,160,731 | 5/1939 | Haeberlin | 15/104.94 |
| 2,887,340 | 5/1959 | Veneko | 15/159 A |
| 3,618,609 | 11/1971 | Glick | 604/1 |

FOREIGN PATENT DOCUMENTS 490124  8/1938  United Kingdom ............ 15/159 A

OTHER PUBLICATIONS

IBM, Technical Disclosure Bulletin, vol. 9, No. 4, Sep. 1966, p. 417.
Brushes International, vol. 60, No. 709, Jan. 1, 1974, pp. 23, 24.

*Primary Examiner*—Peter Feldman
*Attorney, Agent, or Firm*—Jacobs & Jacobs

[57] ABSTRACT

An implement for removing dental plaque and massaging gums in a form of a slender rod-like body of appropriate length comprising a fibrous structure obtained by bundling or bundling and bonding a plurality of fibers such as synthetic fibers in a longitudinal direction and a shell layer on the outer peripheral section of the fibrous structure, the shell layer is partly cut or ground to expose the fibrous layer in the interior thereof to form a brushing section, the fibrous layer may contain such as hygienically harmless alkali substances, surfactant, bactericide, deodorant, perfumes or the like.

5 Claims, 6 Drawing Figures

DENTAL IMPLEMENT FOR REMOVING PLAQUE AND MASSAGING GUMS

BACKGROUND OF THE INVENTION

Dental plaque is considered as the cause of dental caries and paradental diseases in the dental treating and hygienic fields, and also for massaging gums.

As well known, a tooth brush has been used conventionally as the typical implement of this sort, in general. Said plaque starts first from deposition of a thin film essentially comprising protein and carbohydrate over the surface of enamel of tooth, to which then oral bacteria are attached and proliferated to form the plaque which consists mainly of bacteria and the metabolic products thereof. Said plaque can be removed from the major surface area of teeth by brushing after every meal but there are the parts where the effect of brushing cannot reach and where plaque is accumulated. Plaque not only becomes the direct cause of dental caries and inflammations of gums, but when calcification progresses, it turns into dental calculus and is deposited further firmly. And moreover, since said plaque and dental calculus are considered to be one cause of the onset and exacerbation of alveolar blennorrhea, a paradental disease, complete healing from which is quite difficult, with the view of dental hygiene, removal of plaque has a quite significant meaning.

As the implements for removing the plaque deposited interdental or cervical parts, on the other hand, such a tooth pick-like implement made of wood and having a thickness capable of being inserted between teeth (FIG. 1), a linear synthetic filament or an implement with a bow-like section where the filament is stretched (FIG. 2), or a tooth brush with a conical projection of rubber with a pointed tip provided at the end of the rod (FIG. 3) have been put on market, and the patients who visit dentists are instructed to remove plaque by rubbing daily the interdental and cervical parts by using such implements.

However the wooden tooth pick-like impelement has not a sufficient strength at the tip for rubbing the narrow interdental parts, and if the strength be increased by thickening the tip, it cannot be applied for the narrow interdental part. On the other hand, the method of rubbing the interdental parts by use of the thread-like synthetic filament with the fingers of both hands has difficulty in spreading widely because of the troublesome handling, and the implement with the section where the filament is stretched requires a skill to effect satisfactory rubbing with it, and it cannot be said a satisfactory implement for removing plaque correctly. On the other hand, it is a matter of course that the rubber projection at the end of tooth brush has a difficulty in rubbing with it the narrow interdental part, and both of these implements are unsatisfactory as the implement for removing plaque. Thus the appearance of an implement with which removal of plaque can readily be effected daily by the patient himself has been anticipated.

DESCRIPTION OF THE INVENTION

The object of the present invention is to improve such deficient points in handling the conventional implements for the purpose and to provide an implement highly effective for removal of plaque and massaging gums produced in a commercial scale and offered at a low cost.

The implement of the present invention for removing plaque and massaging gums is characterized by the features that on the outer peripheral section of a fibrous structure obtained by bundling or bundling and bonding a plurality of fibers in a longitudinal direction, a shell layer having a greater physical strength at least as compared with that of the fibrous layer in the interior section is formed to form a slender rod-like body of appropriate length, then the shell layer is partly cut or ground to expose the fibrous layer in the interior thereof to form a brushing section.

According to the structure of the invention of the present application, it is possible to produce readily and in a large quantity the various implements having the merits as we are setting forth below by the arts of manufacture known by, for example, Japanese Patent Application Publication No. 39889/1970, U.S. Pat. No. 3,558,392, or U.S. Pat. No. 3,464,775, etc. relating to the liquid-effusing elements for writing instrument.

BRIEF DESCRIPTION OF THE DRAWING

FIG. 4-B shows the tip section of the front view thereof. The mark 1 is the tubular shell layer, and 2 shows the nylon filament tow.

Hereinafter we explain the present invention further in detail in actual examples.

EXAMPLE 1

Figure 1:
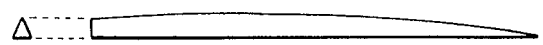
FIG. 1 shows a wooden, tooth pick-like implement that has been conventionally used.
Figure 2:
FIG. 2 shows a conventional implement where synthetic fibers are stretched in a bow-like fashion on a plastic supporting body.
Figure 3:
FIG. 3 shows a conventional implement where at one end of a tooth brush, a conical projection of rubber with a pointed tip is provided.
Figure 4:
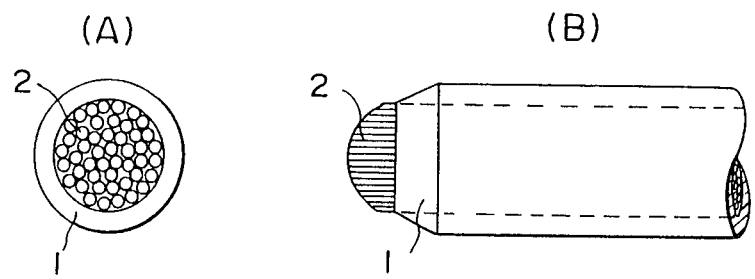
FIG. 4-A shows a cross-section of the stem section of the implement of the present invention as described in Example 1.

Polyacetal resin was melt-coated over a nylon filament tow of 8000 denier comprising filaments of fineness 10 denier to form a tubular shell layer, and at the same time, a continuous fibrous structure of a diameter 2 mm was formed, and one end of a slender rod-like body obtained by cutting the above structure to the length of 25 mm was cut into a semispherical shape as shown in FIG. 4 to expose the fibrous layer, then it was subjected to sterilizing treatment to obtain an implement for removing plaque.

When the implement was used for healthy young people whose teeth had almost no interstices inbetween, the fine fibrous layer where the filaments ran uniformly lengthwise got untied adequately to readily massage the interdental parts and gums so that the plaque in the portions where the bristles of a tooth brush could not reach to massage could be well cleaned up.

EXAMPLE 2

Figure 5:
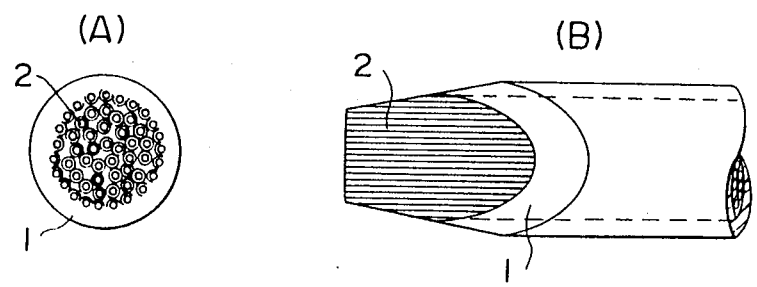
FIG. 5 shows the implement of Example 2, FIG. 6 that of Example 3 respectively, where A is a cross section of the stem section and B is the tip section of the front view thereof; the mark 1 shows the shell layer of the respective implement, 2 shows the filament tow thereof.

A composite filament tow of polyamide-polyester of 15000 denier comprising filaments of fineness 15 denier was heated and compressed and the surface layer was melt-molded to form a shell layer and thereby to form a continuous fibrous structure of a diameter 2 mm, then the structure was cut into the length of 30 mm, and one end of the thus obtained slender rod-like body was cut or ground into the shape as shown in FIG. 5 to expose the fibrous layer, then it was subjected to sterilizing treatment to obtain an implement for removing plaque.

The implement thus obtained had a brushing section with the softness much softer than that of the implement of Example 1, and excellent flexibility in the section reaching the shell layer, and it was found to have a high plaque-removing and easy massaging effect.

EXAMPLE 3

Figure 6:
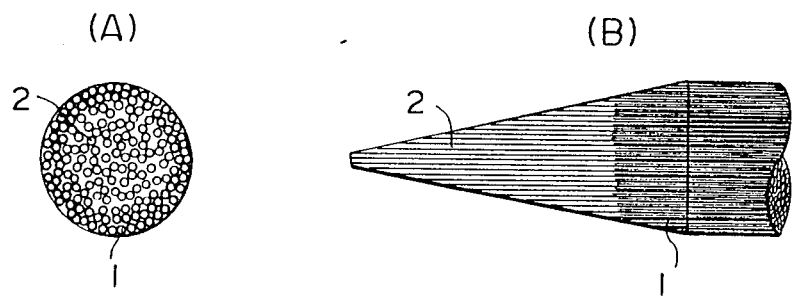

A polyester filament tow of 9000 denier comprising filaments of fineness 3 denier was heated and compressed, then a thermosetting adhesive solution was impregnated therein, and it was dried and cured by heating to form a shell layer, and formed into a continuous fibrous structure of a diameter 1.5 mm. The structure was then cut into the length of 40 mm, and one end of the thus obtained slender rod-like body was cut or groud into a conical shape as shown in FIG. 6 to expose the interior fibrous layer, and subsequently it was subjected to sterilizing treatment to obtain an implement for removing plaque.

When the implement was used for middle-aged and old patents with progressed paradental diseases, where pocket formation in the gums and gingival retraction caused by absorption of alveolar bones (i.e. erosion) were observed, it was found to be a massaging implement with high plaque-removing effect, which made it quite easy to massage deep in the interdental portions, and had the softness favorable in contact with teeth and gum surfaces due to the fineness of the filaments in its brushing section, and good flexibility and untying characteristics, and exerted satisfactory massaging effect to rub the gums attacked by paradental diseases and at the same time to activate capillary vessels.

Since the implement of the invention of the present application has the filaments bundled lengthwise, it brings forth a capillary action among the filaments so that it is also possible to let it hold in the interstices among the filaments chemicals and perfumes suitable for the purposes.

For example, when such alkali substances as sodium bicarbonate that is hygienically harmless and facilitates removal of plaque, a surfactant, a germicidal such as chlorohexidine salt that acts on the plaque-forming cause bacteria such as *Streptococcus mutans*, a deodorant such as sodium copper chlorophyllin, and a perfume such as Kuromojioil, respectively alone or in combination of plural kinds, in the form of an aqueous solution or a solution of an organic solvent, are absorbed in the fibers during the processing of after molding and dried, the chemicals are effused by means of saliva in the use and exert the respective effects.

Furthermore, since the implement of the invention of the present application has the structure where the interior fibrous layer is coated with an outer peripheral shell layer having a greater physical strength as compared with that of the interior fibrous layer, it has the merit that the fiber material having the physical properties, thickness and the amount of the fibers can be selected suitable for the purposes for said fibrous layer forming the brushing section. As for the fiber material, ceramic fibers in a broad sense, metal fibers such as stainless steel, and the synthetic fibers belonging to the respective types such as polyamide, polyester, polyvinyl alcohol, polyacetal, polyolefin, polyurethane, etc. may be usable, and in case of inorganic high molecular fibers and metal fibers, the fibers of the fineness less than $30\mu$, and in case of synthetic high molcular fibers, that of less than 20 denier are used.

In regard to the modes for forming the shell layer as shown in the respective Examples, the mode of Example 1 can be employed for the fiber material of any type and the shell layer-forming material can also be selected appropriately from the thermoplastic synthetic resin molding materials commercially available in general. The mode of Example 2 is, on the other hand, suitable for the synthetic high molecular fiber materials having good heat-melting properties, whereas the mode of Example 3 is suitable for the synthetic high molecular fiber materials subjected to crimping processing, and the material can also be selected and used appropriately from the adhesives and coating materials as well as from the molding materials.

Still-further, since the brushing section of the implement of the invention of the present application is formed by cutting or grinding the shell layer to expose the interior fibrous layer, the tip variant in shape can readily be obtained, and thus it has the merit that the curves at the tip, diameter and thickness may be formed various within the extent of the object of use. Ordinarily, the most desirable diameter of the tip is in the range from 0.1 to 2 mm, and the length from 1 to 5 mm. For the stem, any size of diameter and length will do so long as they are within the ranges one can readily pick it up, and the suitable sizes are generally the diameter from 0.8 to 3 mm and the length from 25 to 50 mm. But the diameter and the length indicate only appropriate examples and the modes of the present invention are not limited thereby at all.

As we have so far set forth in detail, the implement for removing plaque and massaging gums of the structure of the present invention has the effects and merits that the product with a brushing section having physical properties most suitable for teeth and paradental tissue can be provided at a low cost and in a large quantity.

We claim:

1. A dental implement for removing plaque and massaging gums, which comprises a slender rod-like body in the form of a toothpick having an inner fibrous structure formed of a plurality of fibers arranged in a longitudinal direction, and an elongated shell layer consisting essentially of a thermally melt-adhered thermoplastic resin surrounding and in direct contact with said inner fibrous structure and having a greater physical strength as compared with that of said inner fibrous structure, said shell layer being partly cut or ground down so as to terminate remote from an end of said inner fibrous structure to expose said fibrous structure and thus to provide a brushing section.

2. A dental implement for removing plaque and massaging gums as described in claim 1, characterized in that said shell layer is tubular.

3. A dental implement for removing plaque and massaging gums as described in claim 1, characterized in that the fibrous structure of the brushing section is formed from synthetic fibers.

4. A dental implement for removing plaque as described in claim 2, characterized in that the fibrous structure of the brushing section is formed from inorganic high molecular fibers or metal fibers.

5. A dental implement for removing plaque and massaging gums as described in claim 1, characterized in that the fibrous structure contains one or more kinds of hygienically harmless alkali substances, surfactant, bactericide, deodorant, perfume or the like.

* * * * *

UNITED STATES PATENT AND TRADEMARK OFFICE
CERTIFICATE OF CORRECTION

PATENT NO. : 4,462,136
DATED : July 31, 1984
INVENTOR(S) : SHUNICHI NAKAO ET AL.

It is certified that error appears in the above-identified patent and that said Letters Patent are hereby corrected as shown below:

On the title page

In item 73, the name of the first Assignee should read -

-- SHOWA YAKUHIN KAKO CO. LTD. --

Signed and Sealed this

Twenty-sixth Day of March 1985

[SEAL]

Attest:

DONALD J. QUIGG

Attesting Officer

Acting Commissioner of Patents and Trademarks